US006755858B1

(12) United States Patent
White

(10) Patent No.: US 6,755,858 B1
(45) Date of Patent: Jun. 29, 2004

(54) PROSTHETIC CORNEAL GRAFT AND METHOD

(76) Inventor: Thomas C. White, 1127 Holly Dr., Sioux Falls, SD (US) 57105

( * ) Notice: Subject to any disclaimer, the term of this patent is extended or adjusted under 35 U.S.C. 154(b) by 0 days.

(21) Appl. No.: 09/545,532

(22) Filed: Apr. 7, 2000

(51) Int. Cl.[7] .................................................. A61F 2/14
(52) U.S. Cl. ..................................... 623/5.12; 623/5.13
(58) Field of Search ............................. 623/5.11–5.16, 623/FOR 104; A61F 2/14

(56) References Cited

U.S. PATENT DOCUMENTS

| | | | | |
|---|---|---|---|---|
| 4,470,159 A | * | 9/1984 | Peyman | 623/5.11 |
| 4,612,012 A | | 9/1986 | White | 623/5 |
| 4,772,283 A | | 9/1988 | White | 623/5 |
| 5,030,230 A | | 7/1991 | White | 623/5 |
| 5,139,518 A | | 8/1992 | White | 623/5 |
| 5,269,812 A | | 12/1993 | White | 623/5 |
| 5,459,177 A | * | 10/1995 | Miyakoshi et al. | 523/111 |
| 5,489,301 A | * | 2/1996 | Barber | 623/5.11 |
| 5,843,185 A | * | 12/1998 | Leon Rolden et al. | 623/5.11 |
| 6,007,575 A | * | 12/1999 | Samuels | 623/1.15 X |
| 6,391,055 B1 | * | 5/2002 | Ikada et al. | 623/5.15 |

FOREIGN PATENT DOCUMENTS

| NL | 8501403 | * 12/1986 |
|---|---|---|

OTHER PUBLICATIONS

Polack, F.M., Visual Restoration with Plastic Corneal Implants, Sep. 1972, Southern Medical J., v. 65; 1118–1122.*

Girard, Louis, Advanced Techniques in Opthalmic Microsurgery, 1981, C.V. Mosby Co., vol. 2, pp. 243–259.*

Maguen et al., Combined Use of Sodium Hyaluronate and Tissue Adhesive in Penetrating Keratoplasty of Corneal Perforations, 1984, Ophthalmic Surgery, vol. 15, pp. 55–57.*

"Fabrication of a Keratoprosthesis" by, Doane et al., Key Towers South, Cornea, vol. 13, No. 2, 1996, pp. 179–84.

* cited by examiner

*Primary Examiner*—David H. Willse
*Assistant Examiner*—Brian E. Pellegrino
(74) *Attorney, Agent, or Firm*—Fredrikson & Byron, P.A.

(57) ABSTRACT

An implantable keratoprosthesis having a central lenticule and a peripheral annulus of corneal tissue. The keratoprosthesis includes a transparent polymeric lenticule having an elongated stem with a generally cylindrical outer surface and a central axis. On one end thereof, the stem carries a dome having a peripheral skirt extending outwardly from the axis beyond the cylindrical surface of the stem. An annulus of corneal tissue has a central bore within which the stem is received, the peripheral skirt contacting and overlying a portion of the corneal annulus adjacent the bore. A portion of the annulus extends outwardly beyond the peripheral skirt for attachment to a surgically prepared cornea. A ring of polymeric material is received over the stem to capture between the ring and the skirt the corneal annulus. The ring is attached to the stem, as by welding and/or by use of a tissue-adherent, biologically acceptable adhesive disposed between the cylindrical surface of the stem and the bore of the annulus to form a strong, liquid-tight seal between the stem and annulus.

13 Claims, 3 Drawing Sheets

PROSTHETIC CORNEAL GRAFT AND METHOD

FIELD OF THE INVENTION

The invention relates to prosthetic devices, and particularly to devices that may be employed to replace damaged corneal tissue.

BACKGROUND OF THE INVENTION

Corneas are subject to a variety of problems which mandate their surgical replacement. For example, corneas may become scratched or scarred, and are subject to effect by various degenerative diseases. Corneal transplants have become quite common in the United States, particularly with the advent of microsurgery. However, corneal transplantation is sometimes not appropriate for patients with intractable keratopathy, or patients in whom corneal transplants fail in standard graft procedures.

Various devices have been proposed for solving these problems. Such devices, referred to keratoprostheses utilize a central lenticule or optic that can be prepared from polymethylmethacrylate or other physiologically acceptable glass or polymeric material. A device of this type is shown in White, U.S. Pat. No. 4,612,012, issued Sep. 16, 1986, and White, U.S. Pat. No. 5,030,230, issued Jul. 9, 1991.

Another keratoprosthesis having a collar button design is shown in Doane, M. G., Dohlman, C. H. and Bearse, G., *Fabrication of a Keratoprostheses, Cornea* 1996: 179–184. The latter device is pre-assembled (i.e., before being placed into tissue) and utilizes a mushroom-shaped plastic member having a threaded post, the cap portion of which fits against the front of a patient's cornea. A second threaded part is threaded onto the post to complete the construction. In use, a small hole is trephined through the center of a patient's cornea, followed by a limbal incision and a radial connecting slit. The device is slid into place with the rim of corneal tissue captured between the two plates; the cornea is hence fitted around the threaded post between the anterior and posterior plates. The incisions are then sutured shut, but inasmuch as the portion of the incision between the plates cannot readily be sutured shut, it is extremely difficult if not impossible to achieve the liquid-tight junction between the device and the cornea that is essential for success.

In the latter device, the threaded post portion, of course, must be sufficiently long as to extend through the thickness of the patient's cornea and for a sufficient distance beyond so as to fully receive the internally threaded second member and to avoid cross-threading. The iris of the eye commonly is spaced posteriorly of the posterior surface of the cornea by only a very short distance, e.g., about 1.7 mm, and hence there is a concern that the post may extend too deeply into the eye so that the iris and lens and sometimes parts of the vitreous need to be surgically removed. Moreover, since the parts are simply threaded together, there is always the potential for unthreading of the device and hence loss of the interior portion—the second portion—into the anterior chamber, causing extrusion of the mushroom-shaped portion with consequent severe problems.

It would be desirable to provide a keratoprosthesis that could readily be attached to the corneal rim of a patient's eye in a water-tight manner, that would avoid immune rejection problems, that would provide a lenticule not subject to extrusion from the patient's eye, and that would not protrude posteriorly any significant distance into the anterior chamber.

SUMMARY OF THE INVENTION

I have found that a transparent, polymeric lenticule having an elongated stem having at one end thereof a dome-shaped extension having an outwardly extending peripheral skirt can be securely fixed within a bore formed in undenatured corneal or other appropriate tissue in a strong and leak-free manner without requiring any radial incision extending into the bore.

In one embodiment, the invention provides a method for installing, in a liquid tight manner within a bore formed in the cornea and having no radial incision intercepting the bore, a transparent, polymeric lenticule having an elongated, smooth (that is, unthreaded) stem bearing at one end thereof a dome-shaped extension having an outwardly extending peripheral skirt. The stem is placed within the bore with the peripheral skirt contacting and overlying the cornea. A ring, preferably of polymeric material, is received coaxially about the end of the stem that protrudes posteriorly from the cornea and is advanced up the stem to firmly capture between it and the skirt the corneal tissue. The ring is attached to the stem, as by use of an adhesive or by solvent or ultrasonic welding or the like, to form a liquid-tight seal between the lenticule and the cornea.

In another embodiment, the invention relates to an implantable lens comprising a transparent, polymeric lenticule having an elongated stem with a generally cylindrical outer surface and a central axis, the stem bearing at one end thereof a dome-shaped extension having a peripheral skirt extending outwardly from the axis beyond the cylindrical surface of the stem. The lens includes an annulus of undenatured tissue, preferably corneal tissue, having a central bore free from intersecting radial incisions and within which the stem is received. The peripheral skirt of the lenticule contacts and overlies a portion of the tissue annulus adjacent the bore, with a portion of the annulus extending outwardly beyond the peripheral skirt for attachment to the rim of a surgically prepared cornea. A ring, preferably of polymeric material, is received coaxially about the second end of the stem and is attached to the stem, as by use of an adhesive or by solvent welding or ultrasonic welding or the like, to capture the tissue annulus between it and the peripheral skirt of the lenticule. The seal thus provided between the lenticule and the tissue annulus is strong and liquid tight.

In a preferred embodiment, a tissue-adherent, biologically acceptable adhesive is disposed between the cylindrical surface of the stem and the bore within which it is received, and forms a strong, liquid-tight seal. The tissue annulus may, if desired, be provided with a series of partial perforations within which the adhesive may flow to provide improved gripping power to the tissue annulus.

In another embodiment, the invention relates to a method for forming an implantable lens prothesis. A transparent polymeric lenticule having an elongated stem with a generally cylindrical outer surface and a central axis is provided, the stem bearing on one end a dome having a peripheral skirt extending outwardly from the axis beyond the cylindrical surface. Implantable tissue (which may be corneal or scleral tissue of the patient, as described further below or which may be from a donor), is provided with a central bore within which the elongated stem is received, the bore being free of intersecting radial incisions. A ring, preferably of polymeric material, is placed coaxially about the second end of the lenticule stem to firmly capture the tissue between the ring and the peripheral skirt, and the ring is adhered to the stem, as by use of solvent, thermal or ultrasonic welding and/or through use of an adhesive. Preferably, a suitable adhesive is disposed between the cylindrical surface of the stem and the bore of the tissue annulus to form a strong, liquid tight seal between the stem and annulus. It is of course desirable, to further avoid rejection problems, to employ an annulus of corneal tissue harvested from the patient himself or herself, and in yet another preferred embodiment of the method, the implantable lens is assembled upon a flap of cornea of the patient that has not been severed completely from the remainder of the cornea.

In the above-described embodiments, removal of the epithelium and preferably also the endothelium and Descemet's Membrane, from a corneal tissue annulus in those areas that are to be adhered to the lenticule and polymeric ring enable the adhesive to contact the corneal stroma only.

DESCRIPTION OF THE PREFERRED EMBODIMENT

Figure 8:
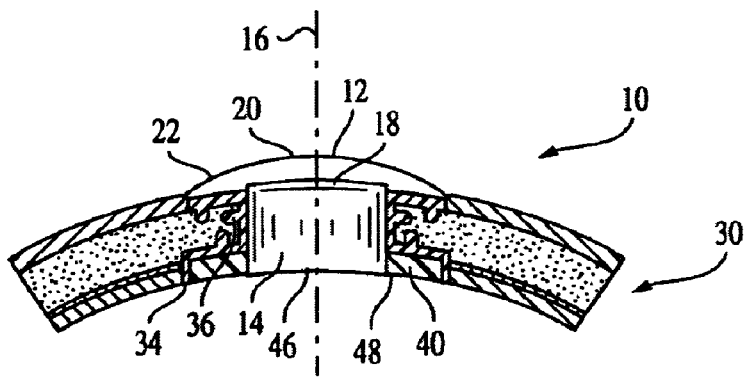
FIG. 8 is a view, in partial cross-section, an assembled keratoprosthesis.

Referring first to FIG. 8, one embodiment of a keratoprosthesis of the invention is shown generally as 10. It includes a lenticule 12 that has an elongated stem 14 having a generally cylindrical surface and a central axis 16. On a first end 18 of the stem is formed a dome 20 having a peripheral skirt 22. An annulus of corneal material, designated generally as 30, is provided with a central bore 32 having a diameter sized to closely receive the stem 14 of the lenticule. An adhesive 34 adhesively bonds the lenticule to the corneal annulus. The lens includes a ring 40, preferably polymeric, the ring having a central opening sized to closely receive the stem 14 of the lenticule and being somewhat flattened so as present a substantial contact surface to the corneal annulus. Note, in FIG. 8, that adhesive 34 bonds the ring 40 to the walls of the cylindrical stem 14 and also bonds confronting surfaces of the peripheral skirt and the ring to the stroma of the corneal annulus.

Although various adhesives may be appropriate for use in the instant invention, it is preferred to use acrylate adhesives in that they tend to bond strongly to collagen stromal tissue and to acrylic (e.g., polymethylmethacrylate) lenticules. A methacryloyloxyethyl trimellitate anhydride adhesive resin, such as that sold under the brand name Amalgam Bond (Parknell), has given excellent results. Adhesives may be two-part adhesives in which curing begins upon mixing the parts together, or the adhesive may be the type which cures upon exposure to ultraviolet light or the like.

The invention is described herein primarily with respect to corneal tissue which is attached to a lenticule in a leak-free manner, and indeed corneal tissue (and preferably corneal tissue of the recipient of the lens) is preferred. However, other undenatured tissue may also be used, such as scleral tissue, fascia, periostial tissue, etc., also preferably from the intended recipient of the lens. In certain of the embodiments described herein, the lenticule is mounted directly to the patient's cornea, either by lifting a flap of corneal tissue to receive the lenticule, or passing the ring member through a slit in the cornea spaced from the bore and attaching the ring member from within the anterior chamber to the stem.

Although adhesive bonding of the lenticule and particularly the lenticule stem to the cornea or corneal annulus is currently preferred in that it provides a liquid-tight seal, it may also be appropriate to utilize other attachment techniques. For example, a preferably flattened polymeric ring may be fitted over the lenticule stem after the latter has been passed through the central bore of the tissue annulus to grip the annulus and trap it between the ring and the peripheral skirt. By axially squeezing together the peripheral skirt and the ring onto the corneal annulus, thus compressing the corneal annulus between the peripheral skirt and the ring, a tight seal may be formed.

Figure 11:
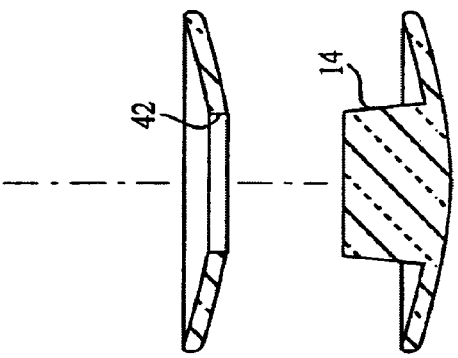
FIG. 11 is an exploded, cross-sectional view of a keratoprosthesis of the invention.

When the ring has thus been properly positioned along the length of the stem, the ring may be fastened to the stem by, for example, solvent welding techniques, ultrasonic welding, etc. The ring preferably has a central bore that provides an inner surface sized to closely receive the lenticule stem, so that surface-to surface contact between the ring and stem. It is preferred that the mating surfaces of the stem and ring be smooth, that is, thread-free, as shown in FIG. 11, although use of threads may be appropriate in some circumstances. It is contemplated that the bore of the ring and the surface of the stem may be provided with identical tapers, such as Morse tapers, to further assure that the ring will not escape from the stem, as also shown in FIG. 11.

Figure 1:
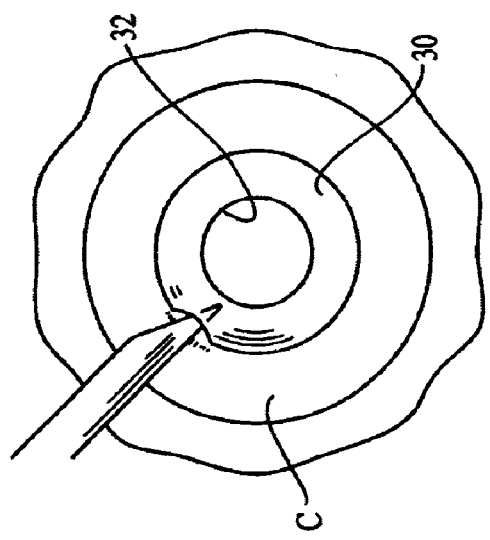
FIG. 1 is a schematic view showing the step in the preparation of a corneal tissue annulus.
Figure 3:
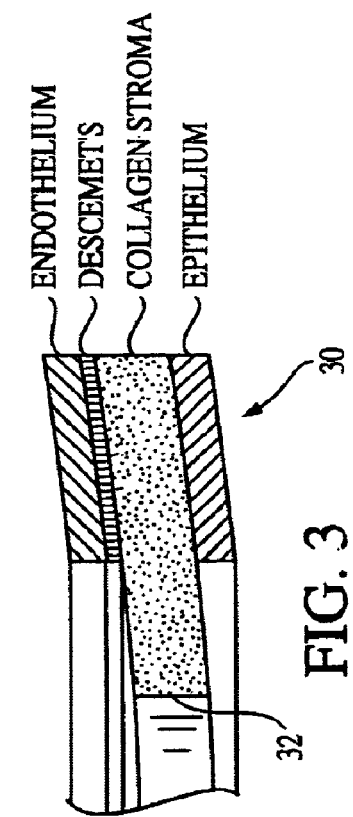
FIG. 3 is a broken-away view similar to that of FIG. 2, but enlarged to show the cornea structure and the removal of structural layers.
Figure 5:
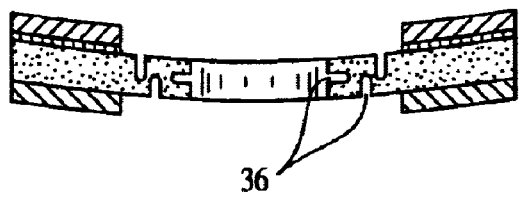
FIG. 5 is a cross-sectional view taken along line 5—5 of FIG. 4.
Figure 6:
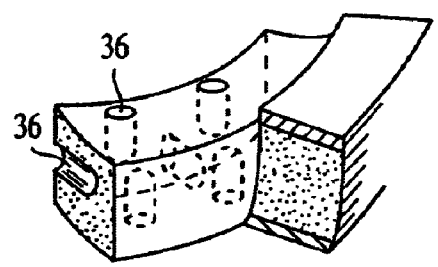
FIG. 6 is an enlarged, broken-away, prospective view showing a portion of the corneal annulus of FIG. 5.

As explained above, the corneal annulus used in a preferred embodiment of the keratoprosthesis of the invention preferably, but not necessarily, comes from the cornea of the patient who is to receive the keratoprosthesis device. FIG. 1 shows the cornea of a patient or donor. The bore 32 is trephined through the thickness of the cornea, following which a surgical procedure utilizing an appropriate cutting instrument such as a trephine, knife or scissors, separates the corneal annulus. FIG. 3, an enlarged view, shows the general structure of the cornea, which includes a central collagen stroma, an outer epithelial layer, and an inner endothelial layer. Between the endothelium and the collagen stroma is Descemet's membrane.

To prepare the cornea or corneal annulus to be mounted to the lenticule, it is important that the epithelium, be removed from those areas of the cornea to which the peripheral skirt of the lenticule 12 and the confronting peripheral surface of the ring 40 are to be adhered, inasmuch as it is desirable to place the adhesive directly in contact with the stroma rather than against this layer. Preferably, but not necessarily, the endothelium and Descemet's membrane also are removed from the cornea adjacent the central corneal bore.

Figure 2:
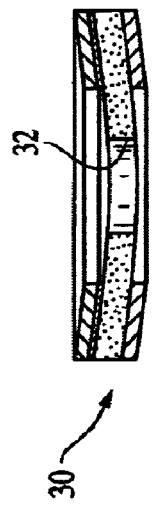
FIG. 2 is a cross-sectional view of a harvested corneal annulus, the layers thereof being of exaggerated thickness to show structure.
Figure 4:
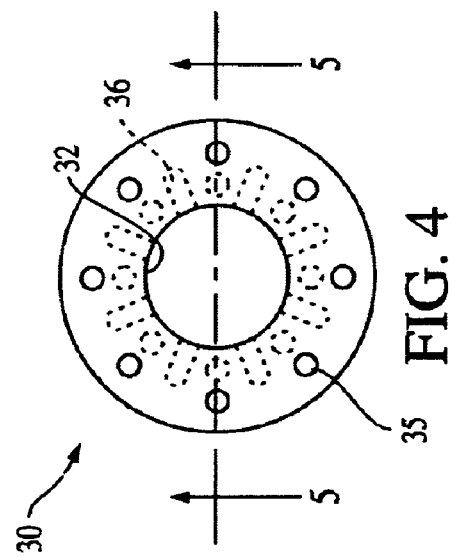
FIG. 4 is view of a prepared corneal annulus showing prepared bores or fissures for the reception of adhesive.
Figure 7:
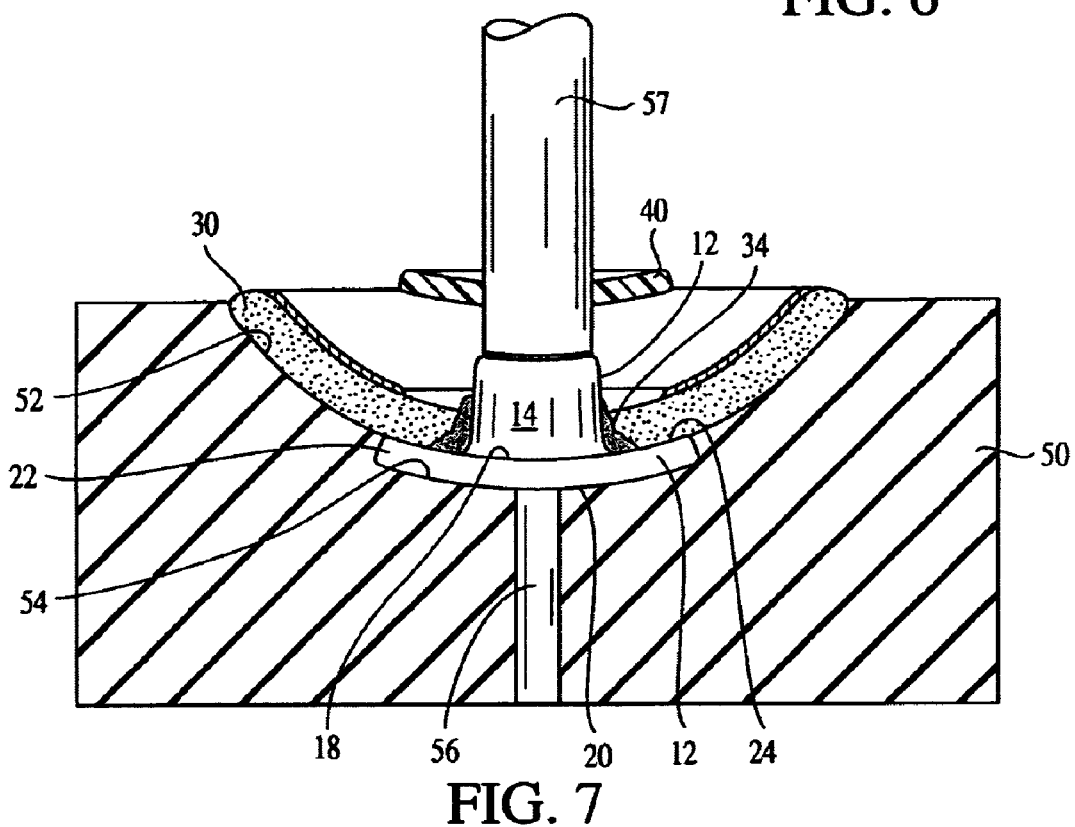
FIG. 7 shows a step in the assembly of a keratoprosthesis of the invention.

As shown in FIG. 4, tiny sewing holes 35 may be formed through the outer periphery of the corneal annulus. Adjacent the interior periphery of the annulus may be formed a series of partial thickness bores or fissures, shown at 36 in FIGS. 4–6 and 8, for the purpose of firmly anchoring the adhesive to the collagen stroma, FIG. 7 shows assembly of one embodiment of a keratoprosthesis of the invention. An assembly block 50, of metal or the like, is provided with a concave upper surface having the same curvature as the corneal surface of the implantable lens. A second, slightly deeper concave surface 54 is provided centrally of the convex surface 52 and has a curvature shaped to receive the domed surface of the lenticule 12. The block 50 is provided with a small, central bore 56. It will be understood that a variety of different assembly blocks 50 may be provided to allow for different curvatures and sizes of keratoprostheses.

In the assembly process, the lenticule 12 is first placed in the recessed surface 54. An adhesive, as described below, may be applied to the upwardly facing surface 24 of the peripheral skirt 22 and to the adjacent surface of the stem 14, and a prepared corneal annulus is then fitted over the stem to bring the surface of the stroma from which the epithelium has been removed into contact with the adhesive. As shown in FIG. 7, the adhesive not only adheres the peripheral skirt to the stroma of the corneal annulus, but also adheres the stroma to the cylindrical walls of the stem 14.

A rod 57, having a diameter desirably slightly less than that of the stem 14, is positioned as shown in FIG. 7 with its lower end pushing downwardly upon the upper end of the stem 14. The rod 57 serves not only to hold the lenticule structure in place, but also facilitates mounting of the ring 40 to the surface of the corneal annulus from which the endothelium and Descemet's membrane has been removed. A suitable adhesive can be placed between the confronting surfaces of the ring 40 and corneal annulus to bond the ring to the annulus.

It will be understood that it is desired to avoid substantial exposure of the adhesive to the anterior chamber, and hence the adhesive that is employed between the ring 40 and the confronting surface of the corneal annulus desirably does not extend all the way to the edge of the ring. It will be noted, from FIG. 8, that the adhesive not only grips the surfaces of the stroma, lenticule and ring, but also may extend inwardly of the small bores or fissures 36 formed in the inner periphery of the annulus. It will also be noted from FIG. 8 that the stem 14 extends posteriorly through the ring 40 and terminates in a surface 46 that is substantially flush with the posterior surface 48 of the ring.

Once the adhesive has set, the resulting implantable lens may be removed from the manufacturing fixture 50 by pushing a slender rod upwardly through the bore 56.

The above description has referred primarily to an embodiment in which the corneal annulus is a separately harvested element of the implantable lens. Fresh corneal tissue is preferred, particularly from the patient, but corneal tissue may be obtained from eye bank corneas as needed, such tissue commonly being stored in a preservative solution such as Optisol, a trademarked product of Bausch & Lomb. The implantable lens, accordingly, may be assembled, as described in connection with FIG. 7, away from the surgical site.

Various cornea handling procedures may be used. For example, a donor cornea first may be devitalized (but not denatured) by placing it in 99% glycerin for a period of time, e.g., 7 days. Upon removal from the glycerin, the cornea is blotted dry and then air dried from 5–7 days. The epithelium is removed centrally, and the tissue is placed endothelial-side up in a concave dish. A central aperture is trephined out to accommodate the lenticule, and an annular strip of endothelium and Descemet's membrane 1.5 mm wide adjacent to the trephined opening may be excised to expose collagen stromal lamellae. Multiple partial thickness perforations of 0.1 mm diameter and 0.3–0.4 mm depth may be made in the anterior and posterior stromal surfaces adjacent the rim. Also, a series of similar perforations may be made into the rim. A lenticule and ring are then bonded, using the above-identified adhesive, to the rim of the corneal annulus, and the resulting product is sterilized by-exposure to cold ethylene oxide gas and then may be packaged for subsequent use.

Figure 10:
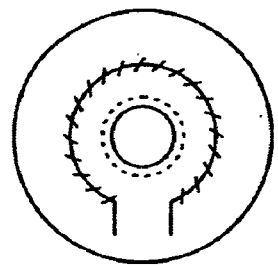
FIG. 10 is a schematic view of the completed surgery following the step of FIG. 9.
Figure 9:
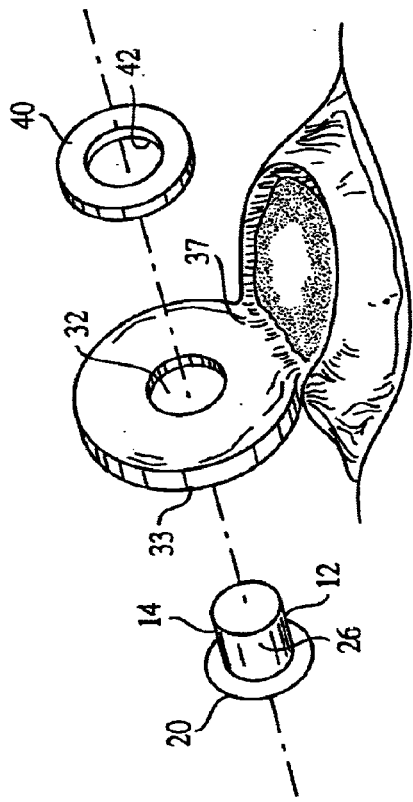
FIG. 9 is a schematic, prospective view of a keratoprosthesis of the invention, as the same is to be mounted to the cornea of a patient from whom the cornea has not been completely severed.

FIGS. 9 and 10 illustrate another embodiment of the invention in which assembly of the implantable lens of the invention involves use of the patient's own cornea to form the corneal annulus and in which the annulus is not severed entirely from the cornea of the patient's eye. Here, assembly of the lens occurs as a part of the surgical procedure. First, a trephine is employed to form a bore 32 centrally of the patient's cornea, and a generally circular cut 33 is made through the thickness of the cornea radially outwardly of the bore 32 but leaving an attached corneal portion 37. The resulting generally annular flap may be raised as shown in FIG. 9, and the endothelium, and optionally the epithelium and Descemets membrane, are surgically removed from the rim of the corneal flap adjacent the bore 32.

A lenticule 12 having an axially extending stem 14 and an outwardly extending, dome-shaped head 20 formed at one end of the stem is inserted through the bore 32. The surface 26 of the stem preferably is smooth and desirably polished. A ring 40, having a smooth and preferably polished interior 42, is received onto the stem 14, capturing the rim of the corneal flap between confronting surfaces of the ring and the dome-shaped head. An adhesive, such as that described above, is preferably employed to promote a liquid-tight seal between the lenticule, ring and corneal rim, although other attachment options such as solvent welding could be used as well or in addition to the adhesive. The flap is then returned to its original position on the cornea and sewn in place, as shown in FIG. 10.

It should be understood that although the lenticule is shown in the drawing as terminating anteriorly adjacent the anterior face of the cornea, if desired, the lenticule may be extended anteriorly so that it may pass through the eyelid of a patient when the underlying eye structure is weak or otherwise unsuitable, the lenticule being installed using known "through the lid" surgical techniques.

In another embodiment utilizing the patient's own cornea, a suitable bore is trephined centrally of the cornea, and corneal stroma is surgically exposed about the bore. The stem of a lenticule is inserted so that the inner surface of the peripheral skirt rests against the anterior stroma of the cornea adjacent the bore. Aqueous humor preferably is been drained from the anterior chamber to provide an air space between the iris and the posterior surface of the cornea. Through an incision made through the cornea but spaced from the bore (that is, not intersecting the bore), a ring as described above may be inserted utilizing suitable instruments into the anterior chamber and is fitted tightly onto the stem, firmly capturing the cornea between it and the overlying lenticule skirt. Adhesive or ultrasonic welding may be employed as needed to ensure a leak-free While particular embodiments of the present invention have been described, it will be understood that various changes, additions and modifications may be made without departing from the spirit of the invention and the scope of the following claims.

What is claimed is:

1. An implantable lens comprising:

a transparent polymeric lenticule having an elongated, unthreaded stem with a generally cylindrical outer surface and a central axis, the stem having first and second ends and having on a first end thereof a dome having a peripheral skirt extending outwardly from the axis beyond said cylindrical surface, an annulus of undenatured tissue having a central bore within which said elongated stem is received and being free of radial incisions intersecting the bore, said peripheral skirt contacting and overlying a portion of said annulus adjacent said bore, with a portion of the annulus extending outwardly beyond said peripheral skirt for attachment to a surgically prepared cornea, and a ring received coaxially about the second end of said lenticule stem and fastened and sealed thereto, the ring having a surface overlying and contacting a confronting portion of said annulus adjacent said stem to squeeze, capture and support said annulus between said ring and said peripheral skirt, the lenticule, stem, ring and tissue annulus providing a liquid tight seal.

2. The lens of claim 1 wherein the cylindrical surface of the stem is smooth, the lens including a biologically acceptable adhesive disposed between said smooth cylindrical surface of said stem and said ring and forming a strong, liquid-tight seal between the stem and ring.

3. The lens of claim 2 including a tissue-adherent, biologically acceptable adhesive disposed between and adhering said ring to a confronting surface of said annulus.

4. The lens of claim 2 or claim 3 in which the annulus of undenatured tissue is corneal tissue and wherein that portion of the corneal tissue annulus that is contacted by adhesive is devoid of epithelium, endothelium, and Descemet's Membrane.

5. The lens of claim 1 wherein said lens is of polymethylmethacrylate polymer.

6. The lens of claim 2 wherein said adhesive is a methacryloyloxyethyl trimellitate anhydride adhesive.

7. The lens of claim 4 wherein surfaces of said corneal annulus contacted by said adhesive have adhesive-receiving perforations formed therein.

8. The lens of claim 2 wherein said adhesive is an acrylate adhesive.

9. An implantable lens comprising:

a transparent polymeric lenticule having an elongated stem with a generally cylindrical, unthreaded outer surface and a central axis, the stem having first and second ends and having on a first end thereof a dome having a peripheral skirt extending outwardly from the axis beyond said cylindrical surface, an annulus of undenatured corneal tissue having a central bore within which said elongated stem is received and being free of radial incisions intersecting the bore, said peripheral skirt contacting and overlying a portion of said corneal tissue annulus adjacent said bore, with a portion of said annulus extending outwardly beyond said peripheral skirt for attachment to a surgically prepared cornea, and a ring received coaxially about the second end of said stem and sealed thereto, the ring having a surface overlying and contacting a confronting portion of said corneal tissue annulus adjacent said stem to capture and compress said annulus of corneal tissue between said ring and said peripheral skirt to provide a liquid tight seal.

10. The implantable lens of claim 9 wherein said ring is affixed to said lenticle stem by thermal welding.

11. The implantable lens of claim 9 or claim 10 wherein said stem is so configured as not to protrude significantly into the anterior chamber of a patient receiving said lens so as to avoid contact with the iris and lens of the patient's eye.

12. The lens of claim 1 or claim 9 wherein the mating surfaces of the ring and stem have identical tapers to assure that the ring will not escape from the stem.

13. The lens of claim 1 or claim 9 wherein the mating surfaces of the ring and stem have Morse tapers.

* * * * *